US010159850B2

(12) United States Patent
Racenet et al.

(10) Patent No.: US 10,159,850 B2
(45) Date of Patent: Dec. 25, 2018

(54) BRACHYTHERAPY CLIP AND APPLICATOR

(71) Applicant: Covidien LP, Mansfield, MA (US)

(72) Inventors: David Racenet, Killingworth, CT (US); Gerald Hodgkinson, Guilford, CT (US); Abhinav Kachru, Woodbridge, CT (US)

(73) Assignee: Covidien LP, Mansfield, MA (US)

( * ) Notice: Subject to any disclaimer, the term of this patent is extended or adjusted under 35 U.S.C. 154(b) by 234 days.

(21) Appl. No.: 14/989,406

(22) Filed: Jan. 6, 2016

(65) Prior Publication Data

US 2017/0189714 A1   Jul. 6, 2017

(51) Int. Cl.
*A61N 5/10* (2006.01)
*A61B 17/072* (2006.01)
*A61B 17/10* (2006.01)
*A61B 17/122* (2006.01)
*A61B 17/128* (2006.01)

(52) U.S. Cl.
CPC ...... *A61N 5/1027* (2013.01); *A61B 17/07207* (2013.01); *A61B 17/10* (2013.01); *A61B 17/122* (2013.01); *A61B 17/128* (2013.01); *A61B 17/1227* (2013.01); *A61N 5/1007* (2013.01); *A61N 2005/1011* (2013.01); *A61N 2005/1019* (2013.01); *A61N 2005/1024* (2013.01); *A61N 2005/1025* (2013.01)

(58) Field of Classification Search
CPC ............... A61N 5/1007; A61N 5/1027; A61N 2005/1011; A61N 2005/1024; A61N 2005/1019; A61N 2005/1025; A61L 317/07207; A61L 317/10; A61L 317/122; A61L 317/1227; A61L 317/128; A61B 17/122; A61B 17/1227; A61B 17/128; A61B 17/10
USPC .......................................................... 600/1–8
See application file for complete search history.

(56) References Cited

U.S. PATENT DOCUMENTS

| 4,754,745 A | 7/1988 | Horowitz |
| 5,030,195 A | 7/1991 | Nardi |
| 5,460,592 A | 10/1995 | Langton et al. |
| 5,626,592 A | 5/1997 | Phillips et al. |

(Continued)

FOREIGN PATENT DOCUMENTS

EP   1126900 A1   8/2001

OTHER PUBLICATIONS

Extended European Search Report for EP 17 15 0346 dated Jul. 13, 2017.

(Continued)

*Primary Examiner* — Navin Natnithithadha
*Assistant Examiner* — Sunita Reddy

(57) ABSTRACT

A surgical implant is provided comprising a biocompatible member configured for securement to an underlying target surgical site and a radiation source integrated into or onto the biocompatible member. The surgical implant may be one of a clip, pin, or coil and the radiation source includes at least one brachytherapy capsule, or other radioactive material incorporated therein or provided thereon. The radioactive material provides a dose of radiation to the target surgical site. The surgical implant may also be formed from titanium, stainless steel or polymers. A surgical applier is provided for allowing a surgeon to apply the implant to a patient's tissue.

19 Claims, 6 Drawing Sheets

(56) References Cited

U.S. PATENT DOCUMENTS

| | | |
|---|---|---|
| 5,713,911 A | 2/1998 | Racenet et al. |
| 5,830,221 A | 11/1998 | Stein et al. |
| 5,906,573 A | 5/1999 | Aretz |
| 6,030,333 A | 2/2000 | Sioshansi et al. |
| 6,146,322 A | 11/2000 | Papirov et al. |
| 6,264,596 B1 | 7/2001 | Weadock |
| 6,293,899 B1 * | 9/2001 | Sioshansi ............. A61N 5/1001 600/3 |
| 6,471,630 B1 | 10/2002 | Sioshansi et al. |
| 6,547,812 B1 | 4/2003 | Hu |
| 6,575,887 B1 | 6/2003 | Schrayer |
| 6,575,888 B2 | 6/2003 | Zamora et al. |
| 6,589,502 B1 | 7/2003 | Coniglione et al. |
| 6,599,230 B2 | 7/2003 | Hastings et al. |
| 6,616,592 B1 | 9/2003 | Rosenthal et al. |
| 6,629,988 B2 | 10/2003 | Weadock |
| 6,749,553 B2 | 6/2004 | Brauckman et al. |
| 6,761,680 B2 | 7/2004 | Terwilliger et al. |
| 6,773,390 B2 | 8/2004 | McDaniel |
| 6,786,858 B2 | 9/2004 | Terwilliger et al. |
| 6,820,318 B2 | 11/2004 | Terwilliger et al. |
| 6,926,733 B2 | 8/2005 | Stinson |
| 6,969,344 B2 | 11/2005 | Drobnik et al. |
| 6,997,862 B2 | 2/2006 | Terwilliger et al. |
| 7,008,368 B2 | 3/2006 | Terwilliger et al. |
| 7,060,020 B2 | 6/2006 | Terwilliger et al. |
| 7,070,554 B2 | 7/2006 | White et al. |
| 7,105,018 B1 | 9/2006 | Yip et al. |
| 7,942,931 B2 | 5/2011 | Gonzalez et al. |
| 7,972,260 B2 | 7/2011 | Wazer et al. |
| 8,061,520 B2 | 11/2011 | Stopek |
| 8,069,980 B2 | 12/2011 | Stopek et al. |
| 8,267,849 B2 | 9/2012 | Wazer et al. |
| 8,292,068 B2 | 10/2012 | Stopek et al. |
| 8,342,376 B2 * | 1/2013 | Surti ................... A61B 17/064 227/175.1 |
| 8,403,946 B2 | 3/2013 | Whitfield et al. |
| 8,454,489 B2 | 6/2013 | Drobnik et al. |
| 8,486,047 B2 | 7/2013 | Stopek |
| 8,529,819 B2 | 9/2013 | Ostapoff et al. |
| 8,551,132 B2 | 10/2013 | Eskridge et al. |
| 8,579,785 B2 | 11/2013 | Shariati |
| 8,939,153 B1 * | 1/2015 | Reicher ................ A61B 5/0031 128/897 |
| 9,198,654 B1 * | 12/2015 | Reicher ................ A61B 5/0031 |
| 2002/0010480 A1 | 1/2002 | Sancoff et al. |
| 2004/0192998 A1 | 9/2004 | Brauckman et al. |
| 2009/0012347 A1 | 1/2009 | Helle et al. |
| 2009/0018535 A1 | 1/2009 | Schechter et al. |
| 2011/0245578 A1 | 10/2011 | Wazer et al. |
| 2012/0125792 A1 | 5/2012 | Cassivi |
| 2014/0066688 A1 | 3/2014 | Cassivi |

OTHER PUBLICATIONS

Partial European Search Report issued in corresponding Application No. EP17150346, dated Mar. 29, 2017, 7 pages.

* cited by examiner

BRACHYTHERAPY CLIP AND APPLICATOR

BACKGROUND

1. Technical Field

The present disclosure relates to surgical implants, clips or fasteners and, more particularly, to surgical low dose brachytherapy implants, clips or fasteners and applicators therefor.

2. Background of Related Art

Generally, brachytherapy is an advanced form of cancer treatment. Specifically, permanent radioactive seeds, sutures, buttresses or the like are placed in or near the cancer site itself, which radioactive seeds, sutures or buttresses emit a relatively low dose of radiation directly to the cancer site while reducing exposure of surrounding healthy tissue to the radiation.

Depending on the underlying cancer to be treated and on the underlying tissue, particular dosimetry guidelines have been developed for the placement of radioactive seeds, sutures or buttresses and for the radiation levels emitted by the radioactive seeds, sutures or buttresses. Generally, the placement of such radioactive seeds, sutures or buttresses are at predefined distances relative to one another in order to enable effective dosimetry. The radioactive sutures and/or buttresses generally include radioactive seeds incorporated therein, which have been placed at fixed, uniform distances to one another.

In view thereof, a need exists, and it is desirous, for surgical brachytherapy implants, clips or fasteners, which may be placed at any desired location relative to the target cancer site. The need also exists, and it is desirous, for an apparatus capable of placing, individually, the surgical brachytherapy implants, clips or fasteners. The brachytherapy implant can be configured as a staple, clip, pin, tack, coil or other implant, to name a few.

The need also exists, and it is desirous, for methods of using the surgical brachytherapy implants, clips or fasteners, and/or the apparatus for placing, individually, the surgical brachytherapy implants, clips or fasteners.

SUMMARY

The present disclosure relates to surgical implants, clips, and/or fasteners.

According to an aspect of the present disclosure, a surgical implant is provided comprising a biocompatible member configured for securement to an underlying target surgical site and a radiation source integrated into or onto the biocompatible member.

The surgical implant may be one of a clip, pin, or coil and the radiation source includes at least one brachytherapy capsule providing a dose of radiation to the target surgical site. The surgical implant may also be formed from titanium, stainless steel or polymers.

According to another aspect of the present disclosure, the clip comprises a deformable backspan, wherein a first leg extends from a first end of the backspan and a second leg extends from a second end of the backspan, and wherein the first leg and the second leg extend substantially in the same direction from the backspan.

A biocompatible radioactive material may be dispersed throughout the surgical implant such that the entirety of the surgical implant irradiates radioactively. The surgical implant may also be coated with one of gold or a colored oxide layer such that the surgical implant is substantially visible in the surgical field during an open procedure or radiographic location.

According to another aspect of the present disclosure, the pin comprises a leg having a proximal end and a distal end and a head extending from the proximal end of the leg at an angular orientation relative to a longitudinal axis of the leg. The pin may include a barb extending from the distal end of the leg and may further include a barb extending from a free end of the head.

According to still another aspect of the present disclosure, the coil comprises a body portion having a first end and a second end opposite the first end, the first end of the body portion having a sharp tissue penetrating point, and the second end having a tang disposed generally inward toward the center of the body portion. The body portion may include approximately 2.5 coils.

According to yet another aspect of the present disclosure, a method of performing a surgical procedure at a target surgical site may be provided. The method may comprise providing a surgical applier loaded with at least one surgical implant, wherein the at least one surgical implant includes a biocompatible member configured for securement to an underlying target surgical site and a radiation source integrated into or onto the biocompatible member, placing the surgical applier adjacent to a first location of the target surgical site, and firing the surgical applier to secure a first surgical implant of the at least one surgical implant to the first location of the target surgical site.

The method may further comprise relocating the surgical applier to a second location of the target surgical site and re-firing the surgical applier to secure a second surgical implant of the at least one surgical implant to the second location of the target surgical site.

The method may further include relocating the surgical applier at a plurality of locations of the target surgical site and re-firing the surgical applier to secure a surgical implant of the at least one surgical implant to each respective location of the plurality of locations of the target surgical site. Additionally, the method may further include relocating the surgical applier at the plurality of locations of the target surgical site and arranging the at least one surgical implant in any configuration, in any pattern, or in any quantity.

A surgical implant of the at least one surgical implant in the form of one of a clip, pin, or coil may also be provided wherein the radiation source is at least one brachytherapy capsule providing a dose of radiation to the target surgical site. A surgical implant of the at least one surgical implant wherein a biocompatible radioactive material is dispersed throughout the surgical implant such that the entirety of the surgical implant irradiates radioactively may also be provided.

According to still another aspect of the present disclosure, a surgical applier is provided. The surgical applier may comprise a handle assembly and an endoscopic shaft assembly rotatably supported on and extending from the handle assembly, the endoscopic shaft assembly configured to articulate off-axis, the endoscopic shaft assembly including an end effector supported at a distal end of the endoscopic shaft assembly, and a plurality of surgical implants loaded therein, wherein a distal-most surgical implant of the plurality of implants is disposable in the end effector and is fired by the end effector upon an actuation of the handle assembly, each surgical implant includes a biocompatible member configured for securement to an underlying target surgical site, and a radiation source integrated into or onto the biocompatible member.

The surgical applier may further comprise a cartridge loaded with the plurality of surgical implants wherein the endoscopic shaft assembly is configured to selectively receive the cartridge. The plurality of surgical implants may be one of a clip, pin, or coil and the radiation source is at least one brachytherapy capsule providing a dose of radiation to the target surgical site.

BRIEF DESCRIPTION OF THE DRAWINGS

The present disclosure will be further described with reference to the accompanying drawings, wherein like reference numerals refer to like parts in the several views, and wherein.

DETAILED DESCRIPTION OF EMBODIMENTS

Figure 1:
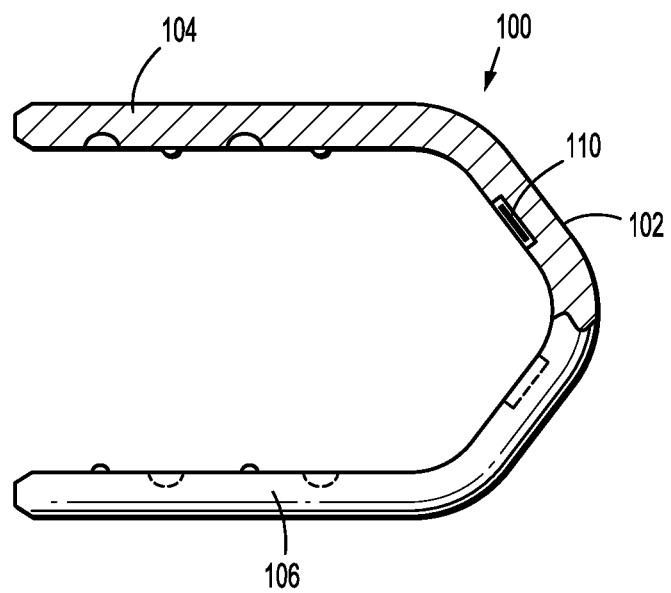
FIGS. 1-5 are plans views of various surgical implants in accordance with embodiments of the present disclosure.

Embodiments of the presently disclosed surgical applying apparatus, and surgical marker or implant, will now be described in detail with reference to the drawings, in which like reference numerals designate identical or corresponding elements in each of the several views. In the drawings and in the description that follows, the term "proximal" will refer to the end of the applying apparatus which is closest to the operator, while the term "distal" will refer to the end of the applying apparatus which is farthest from the operator.

In accordance with the present disclosure, as illustrated in FIGS. 1-5, a surgical implant or clip 100 is provided and includes a backspan or crown 102, a first leg 104 extending from a first end of backspan 102, and a second leg 106 extending from a second end of backspan 102. The first leg 104 and the second leg 106 may extend in the same direction from backspan 102.

Surgical clip 100 may have an unformed condition wherein the first leg 104 and the second leg 106 are parallel, or substantially parallel, to one another and spaced a relative distance from one another. Surgical clip 100 may have a formed condition wherein the first leg 104 and the second leg 106 are parallel, or substantially parallel, to one another and in relative close approximation to one another. In embodiments, first leg 104 and second leg 106 are substantially out of parallel relative to one another.

Surgical clip 100 may be fabricated from a formable material, such as, for example, titanium, stainless steel, or polymers. In this manner, surgical clip 100 may be introduced over a target vessel or tissue while in an unformed condition, and then formed or fastened onto the target vessel or tissue to secure the surgical clip 100 to the target vessel or tissue. It is contemplated that surgical clips 100 may be fabricated from any non-degradable, biocompatible material known by those having skill in the art.

Figure 2:
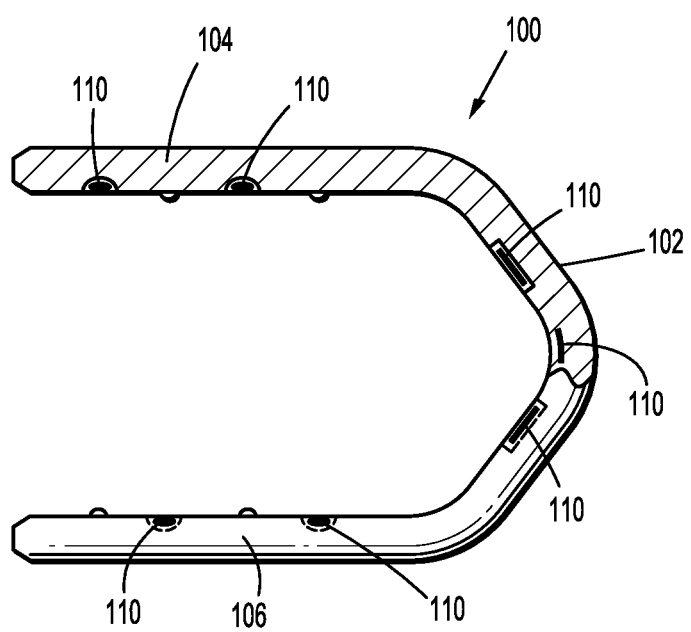

In accordance with the present disclosure, as illustrated in FIG. 1, surgical clip 100 may include a brachytherapy capsule or seed 110, or the like, integrated into backspan 102 thereof. It is contemplated, as illustrated in FIG. 2, that multiple brachytherapy capsules 110 may be integrated into backspan 102 of surgical clip 100. It is further contemplated, as illustrated in FIGS. 3 and 4, that at least one brachytherapy capsule 110 may be secured to an outer surface (e.g., distal, proximal or side) of backspan 102 of surgical clip 100.

Figure 3:
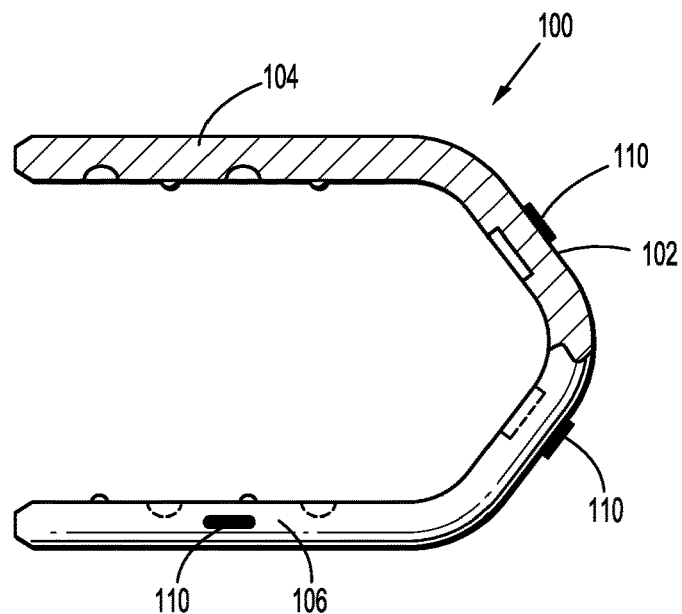
Figure 4:
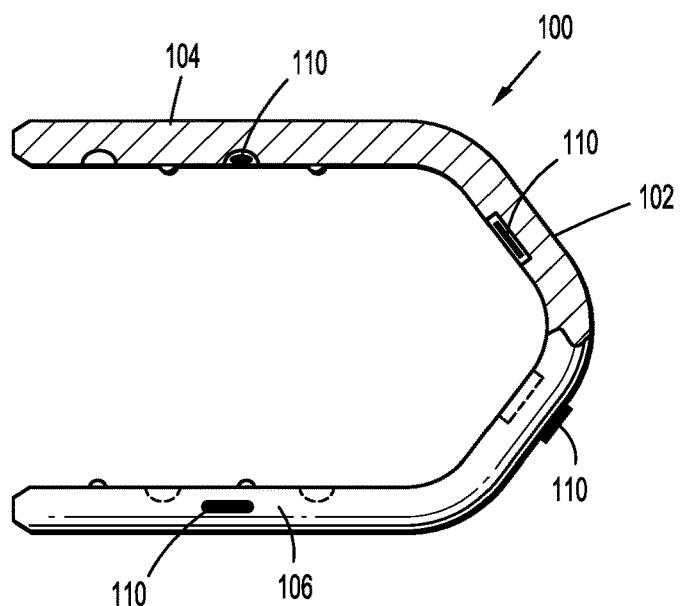

Also in accordance with the present disclosure, as illustrated in FIGS. 2, 3 and 4, surgical clip 100 may include a brachytherapy capsule 110, or the like, integrated into first leg 104 and/or second leg 106 thereof. It is contemplated that multiple brachytherapy capsules 110 may be integrated into first leg 104 and/or second leg 106 of surgical clip 100. It is further contemplated that at least one brachytherapy capsule 110 may be secured to an outer surface (e.g., inboard, outboard or side) of first leg 104 and/or second leg 106 of surgical clip 100.

Any other combinations of placement of brachytherapy capsules 110 along or integration of brachytherapy capsules 110 in surgical clip 100 is contemplated and within the scope of the present disclosure.

Each brachytherapy capsule 100 may include a radioactive material disposed in a shell, or a radioactive material disposed on or throughout a solid body, wherein the radioactive material includes any of a number of radioactive isotopes. Possible low dose isotopes include, but are not limited to, Cesium-131 ($^{131}$Cs), Iridium-192 ($^{192}$Ir), Iodine-125 ($^{125}$I), Palladium-103 ($^{103}$Pd) and Ytterbium-169 ($^{169}$Yb). Therapeutic dosages may range from 80 to 150 Gy depending on the isotope and desired exposure. Surgical clip 100 may have various target energies to provide flexibility in dosimetry planning.

It is envisioned that brachytherapy capsules 100 constitute a radiation source and may be dimensioned so as to produce a particular strength of radiation field therefrom, and/or a particular geometry of the radiation field therefrom.

Figure 5:
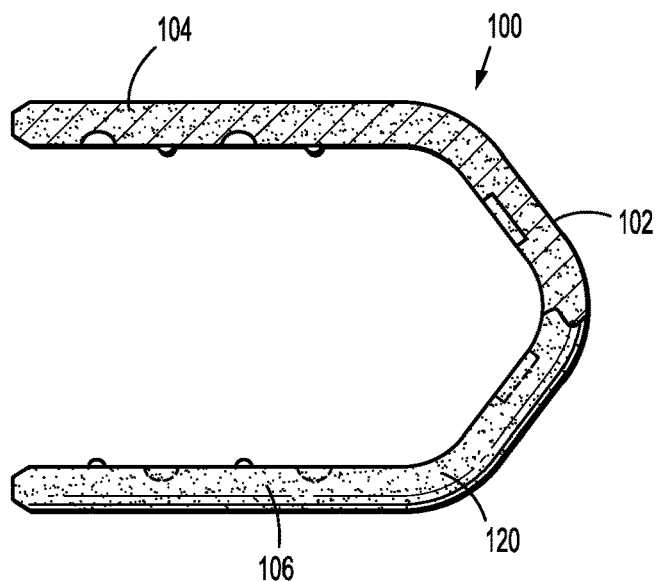

It is further envisioned, as illustrated in FIG. 5, that surgical clip 100 may be processed such that the entirety of surgical clip irradiates radioactively from radioactive material 120 dispersed throughout surgical clip 100. For example, and within the purview of the present disclosure, surgical clip 100 may be processed so as to provide a known degree of radiation field strength. Specifically, in an embodiment, surgical clip 100 may be a polymeric surgical clip fabricated from a radioactive biocompatible material.

In an embodiment, surgical clips 100 are constructed to be visible in the surgical field during either an open or a laparoscopic procedure. Surgical clips 100 may be coated with a material, such as, for example, gold, or coated with a colored oxide layer to make surgical clips 100 relatively more visible. Gold coatings or other coatings may be utilized to enable radiographic location of surgical clips 100 during follow-up procedures. In this manner, surgical clips 100 may serve as fiduciary markers.

In accordance with the present disclosure, by fastening the surgical clip 100 onto a target vessel or tissue, a therapeutic dose of radiation can be applied to a set location and known volume of tissue based on the activity and isotope material of the brachytherapy capsule 110.

Surgical clips 100 serve the purpose of applying a local therapeutic dose of radiation to, for example, a tumor or to a resection site after removal of a cancerous tumor. Surgical clips only require sufficient mechanical strength to hold brachytherapy capsule 110 in place and are not intended to hold tissue structures together.

Surgical clips 100 may be applied or fastened to any number of tissues having a tumorous growth, such as, for example lung tissue, solid organs, gastro-intestinal tissue, and soft tissues.

In accordance with the present disclosure, it is envisioned that surgical clips 100 may be applied separately, and individually, at a location of choice by the attending clinician. Since brachytherapy capsule 110 has a set three-dimensional field of known radiation strength and geometry, multiple individual surgical clips 100 may be applied to the target tissue to enable effective dosimetry.

It is contemplated that surgical clips 100 may be applied or arranged in any configuration, pattern, or quantity to achieve the intended purpose. For example, surgical clips 100 may be arranged in, for example, a straight line, arcuate, triangular, rectangular, circular or other configuration. It is further contemplated that surgical clips 100 may be fastened to the target tissue a uniform distance from one another, various distances from one another, or a combination thereof.

In certain instances, uniform and accurate spacing of surgical clips 100 is desired. For example, if spacing between adjacent surgical clips 100 is not accurate then the desired dosimetry may not be achieved.

In accordance with the present disclosure, while a surgical implant, in the form of a clip 100 has been shown and described in detail, it is contemplated that the surgical implant may include, and is not limited to, a surgical pin, a surgical tack, a surgical coil or the like. As mentioned above, and as contemplated herein, any of the surgical implants may be fabricated from a biocompatible material, such as, for example, titanium, stainless steel or polymers. Likewise, as mentioned above, and as contemplated herein, any of the surgical implants may incorporate therein or support thereon a brachytherapy capsule 110, or may be processed such that the entirety of surgical implant irradiates radioactively.

Figure 6:
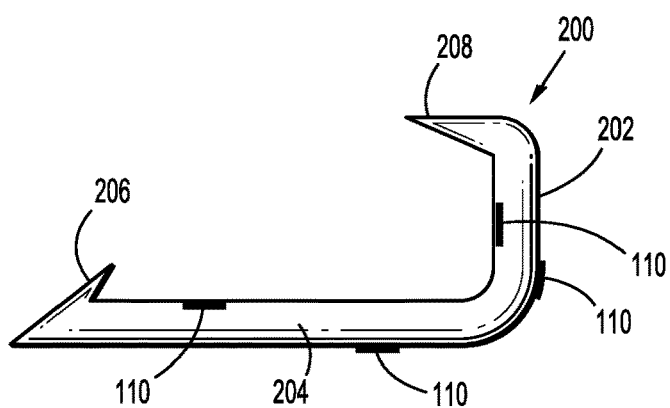
FIG. 6 is a plan view of another embodiment of a surgical implant in accordance with the present disclosure.

For example, with reference to FIG. 6, a surgical implant in the form of a surgical pin is shown and generally designated as 200. Surgical pin 200 may include a leg 204 having a proximal end 204a (not shown) and a distal end 204b (not shown), and a head or arm 202 extending from proximal end 204a. Head 202 may extend orthogonally from a longitudinal axis of leg 204 or at any desired angular orientation relative to the longitudinal axis of leg 204. It is contemplated that surgical pin 200 may include a barb 206 or the like projecting from distal end 204b of leg 204. It is further contemplated that surgical pin 200 may include a barb or tang 208 projecting distally from a free end of head or arm 202, wherein tang 208 functions to help fix an orientation of surgical pin 200 in the target tissue following implantation.

In accordance with the present disclosure, at least one brachytherapy capsule 110 may be disposed within or onto head 202 of surgical pin 200, or may be disposed within or onto leg 204 of surgical pin 200. It is further envisioned that surgical pin 200 may be processed such that the entirety of surgical pin irradiates radioactively from radioactive material dispersed throughout surgical pin 200. For example, and within the purview of the present disclosure, surgical pin 200 may be processed so as to provide a known degree of radiation field strength.

Surgical pin 200 may be fabricated from, for example, titanium, stainless steel or polymers. In an embodiment, surgical pin 200 may be a polymeric surgical pin fabricated from a radioactive biocompatible material. Some examples of non-degradable biocompatible polymers include polyolefins such as polyethylenes and polypropylenes, nylons, polyesters, silicones, polyimides, polymethylmethacrylates, polyurethanes, PTFE, polyethersulfone, polysulfone, PEEK, to name a few.

Figure 7:
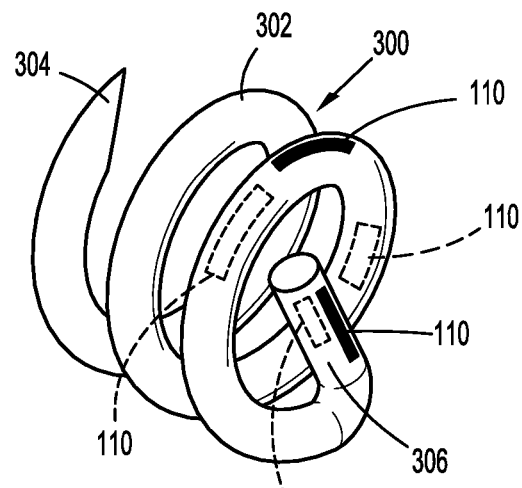
FIGS. 7 and 8 are perspective views of yet another embodiment of a surgical implant in accordance with the present disclosure.
Figure 8:
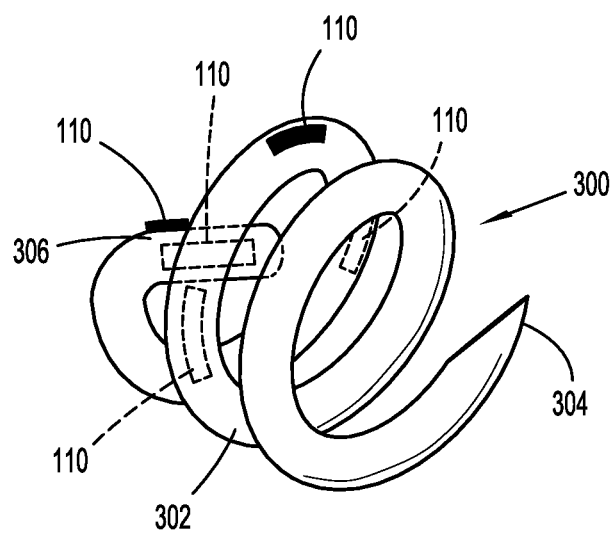

As an additional example, with reference to FIGS. 7 and 8, a surgical implant in the form of a surgical tack or coil is shown and generally designated as 300. Specifically, surgical tack 300 is a helical-shaped coil fastener. Surgical tack 300 is designed for application to tissue by rotating surgical tack 300 into and through the target tissue. Surgical tack 300 generally includes a coil body portion 302, having approximately 2½ coils and terminating in a sharp tissue penetrating point 304. Surgical tack 300 includes a tang 306 at an opposite end of coil body portion 302 from penetrating point 304. Tang 306 extends generally inwardly toward the center of coil body portion 302.

In accordance with the present disclosure, at least one brachytherapy capsule 110 may be disposed within or onto tang 306 of surgical tack 300, or may be disposed within or onto coil body portion 302 of surgical tack 300. It is further envisioned that surgical tack 300 may be processed such that the entirety of surgical tack irradiates radioactively from radioactive material dispersed throughout surgical tack 300. For example, and within the purview of the present disclosure, surgical tack 300 may be processed so as to provide a known degree of radiation field strength.

Surgical tack 300 may be fabricated from, for example, titanium, stainless steel or polymers. In an embodiment, surgical tack 300 may be a polymeric surgical coil fabricated from a radioactive biocompatible material.

While surgical implants in the form of clips, pins and coils have been illustrated and described herein, it is within the scope of the present disclosure that the surgical implants may also include two-part fasteners, tacks, locking hinged fasteners, staples or the like.

Figure 9:
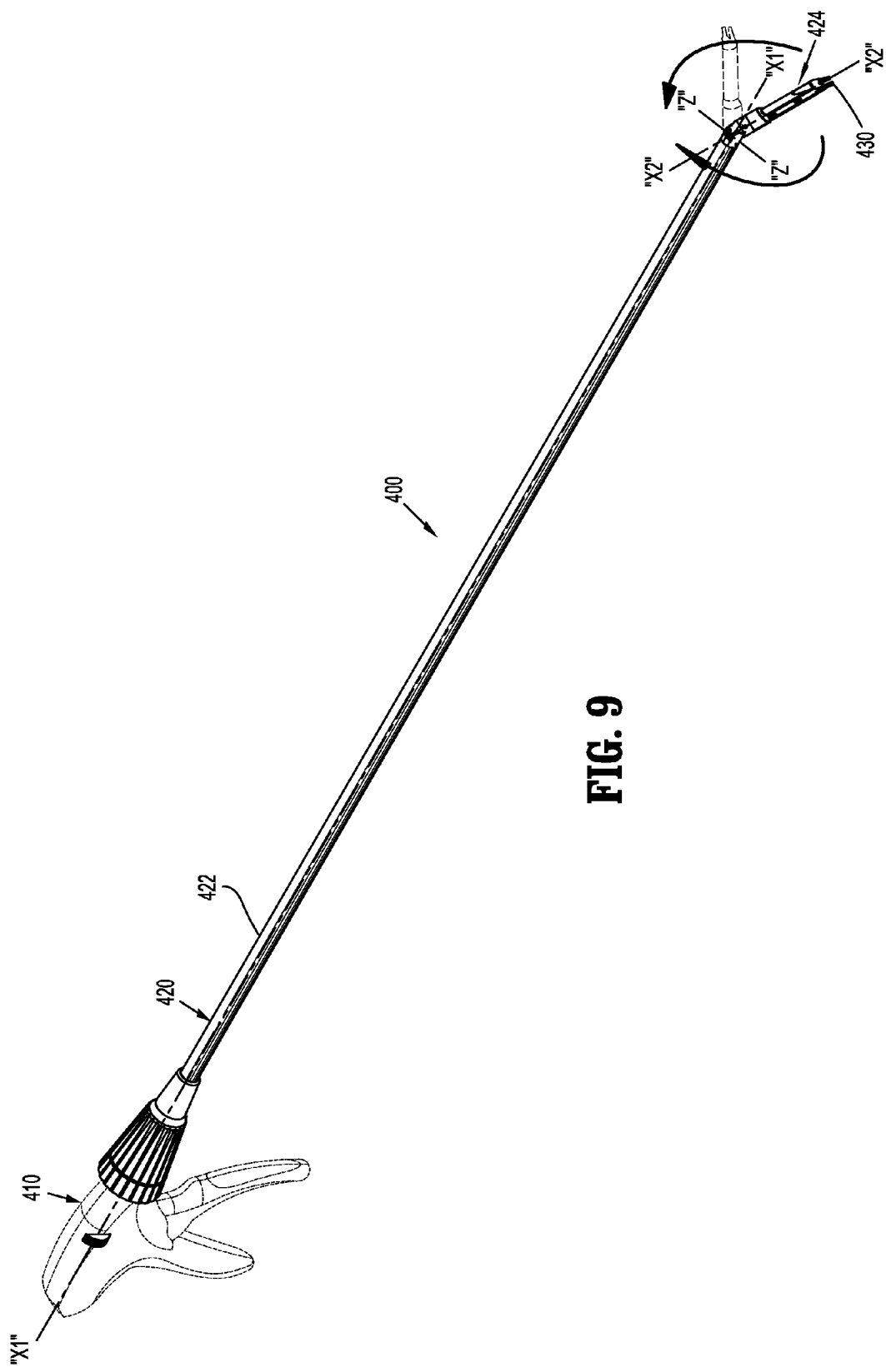
FIG. 9 is a perspective view of a surgical applying apparatus according to an embodiment of the present disclosure, for applying the surgical implants of FIGS. 1-5.

In order to place surgical clips 100 disclosed herein, in accordance with the present disclosure, as illustrated in FIG. 9, a surgical applier 400 is provided. Surgical applier 400 includes a handle assembly 410, and an endoscopic shaft assembly 420 extending from handle assembly 410. Endoscopic shaft assembly 420 is rotatably connected to handle assembly 410 such that endoscopic shaft assembly 420 is rotatable about a longitudinal axis "X1-X1" thereof. Endoscopic shaft assembly 420 may include a proximal portion 422, and a distal portion 424 pivotably connected to proximal portion 422, wherein distal portion 424 may be articulated relative to proximal portion 422.

Distal portion 424 of endoscopic shaft assembly 420 may include a quantity of surgical clips 100 (not shown) pre-loaded therein, or may be configured to selectively receive a cartridge assembly (not shown) which is loaded with a quantity of surgical clips 100 therein. For example, the cartridge assembly may be loaded with ten or fewer surgical clips 100, or any quantity of surgical clips 100.

Distal portion 424 of endoscopic shaft assembly 420 may include a firing and forming mechanism configured to load a single (e.g., distal-most) surgical clip 100 into a pair of jaws 430, and to form the surgical clip 100 loaded into the pair of jaws 430. Surgical applier 400 is configured to fire and form a single surgical clip 100 during a complete firing sequence.

For a more detailed description of the construction and operation of an example of a surgical applier 400, reference may be made to U.S. Pat. No. 8,403,946, the entire content of which is incorporated herein by reference.

Figure 10:
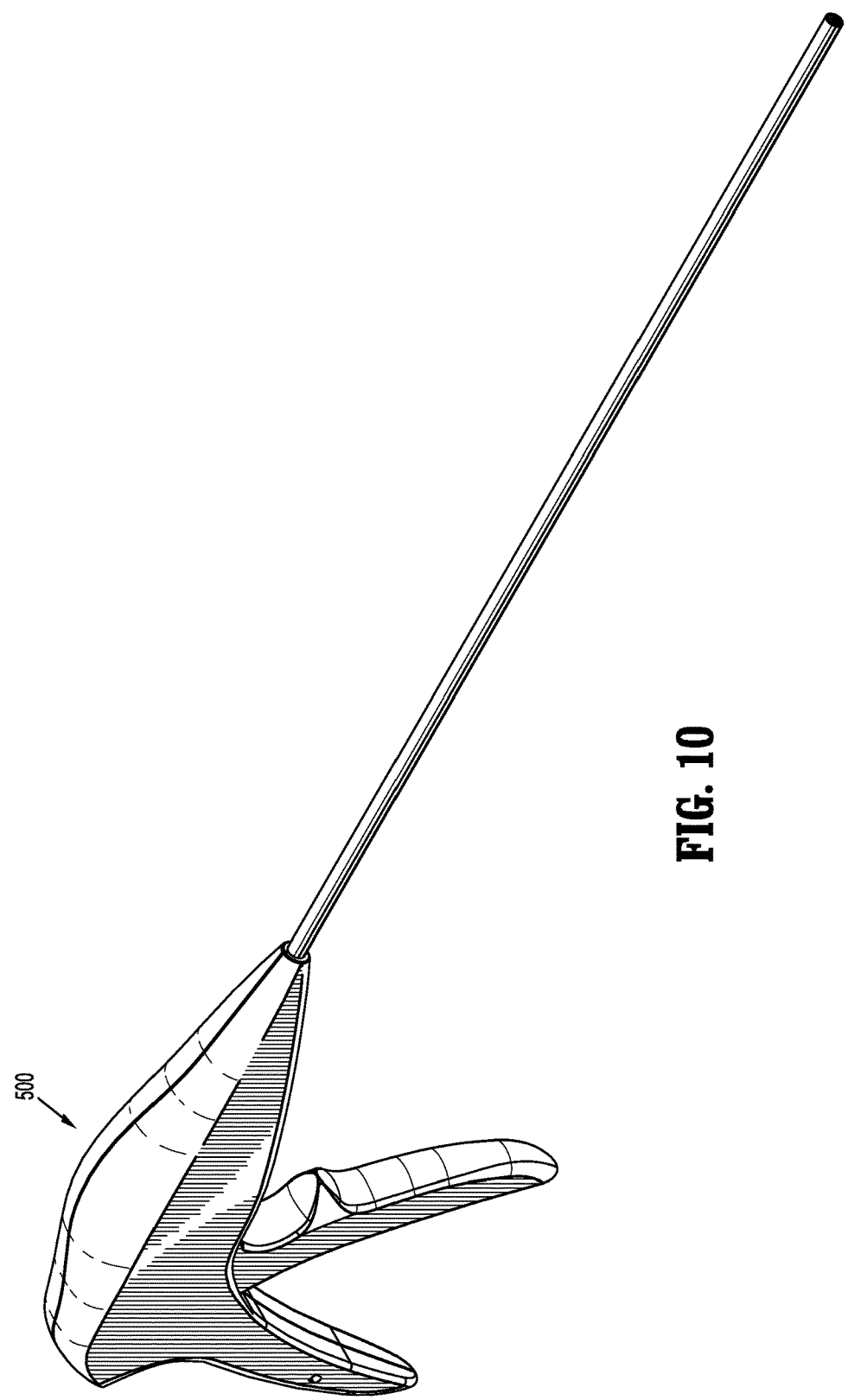
FIG. 10 is a perspective view of a surgical applying apparatus according to another embodiment of the present disclosure, for applying the surgical implants of FIGS. 7 and 8.

In order to place surgical tacks 300, in accordance with the present disclosure, a tack applier 500 (FIG. 10) may be provided which is either pre-loaded with surgical tacks 300, or which may selectively receive a cartridge loaded with surgical tacks 300. The tack applier 500 may be configured to fire or deliver a single surgical tack 300 during a full firing sequence. The tack applier 500 may also be configured to articulate in order to facilitate the firing of surgical tacks 300 therefrom.

For a more detailed description of the construction and operation of an example of a surgical tack applier 500 capable of firing surgical tacks 300, reference may be made to U.S. Pat. No. 5,830,221, the entire content of which is incorporated herein by reference.

In accordance with the present disclosure, the combination of surgical implants and appliers disclosed herein provides the clinician a relatively great deal of flexibility and customization in placing radiation emitting implants (e.g., surgical clips 100, surgical pins 200, surgical tacks 300, etc.) at desired target surgical sites, whereby the applier (e.g., surgical applier 400) is articulatable and/or rotatable to provide the clinician with increased flexibility and precision in placing the radiation emitting implants.

It is contemplated for example, that a geometry of surgical clip 100, surgical pin 200 and surgical tack 300; and a geometry of a tip (e.g., the pair of jaws, etc.) of a surgical applier may be optimized to work together as location guides to optimally place surgical clip 100, surgical pin 200 and/or surgical tack 300 adjacent to one another, wherein the brachytherapy capsule 100 has a known geometry and radiation field strength, to achieve effective dosimetry.

In accordance with the present disclosure, the location of placement of surgical clips 100, surgical pins 200 and/or surgical tacks 300 is not limited to a predefined geometry, pattern, density, or the like. In particular, as mentioned above, surgical clips 100, surgical pins 200 and/or surgical tacks 300 may be fastened to a target tissue site in any geometry, pattern and/or density, as the clinician desires or needs.

By way of example, the ability to fasten surgical clips 100, surgical pins 200 and/or surgical tacks 300, to a target tissue site (e.g., lung tissue in a lung resection procedure), in any geometry, pattern and/or density, may be quite useful in a lung cancer patient, where many lung cancer patients suffer from impaired lung volume and cannot tolerate unnecessary loss of lung volume, and may need multiple rows of brachytherapy sources to ensure treatment of an inadequately narrow surgical margin.

In any of the embodiments disclosed herein, the surgical implants (e.g., surgical clips 100, surgical pins 200 and/or surgical tacks 300) may be incorporated into, or configured for use with, devices that are part of a powered surgical system or robotic surgical system.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. A surgical implant, comprising:
   a pin configured for securement to an underlying target surgical site, the pin including:
      a leg defining a longitudinal leg axis and having a proximal end and a free distal end;
      a head extending from the proximal end of the leg along a longitudinal head axis disposed at an angular orientation relative to the longitudinal leg axis and terminating at a free end;
      a first barb extending from the free distal end of the leg at an angular orientation relative to the longitudinal leg axis: and
      a second barb extending from the free end of the head at an angular orientation relative to the longitudinal head axis; and
   a radiation source integrated into or onto the pin;
   wherein the longitudinal head axis and a longitudinal axis of the second barb define an obtuse interior angle therebetween.

2. The surgical implant of claim 1, wherein the radiation source includes at least one brachytherapy capsule providing a dose of radiation to the target surgical site.

3. The surgical implant of claim 2, wherein the at least one brachytherapy capsule is disposed within the leg or the head of the pin.

4. The surgical implant of claim 2, wherein the at least one brachytherapy capsule is disposed on an outer surface of the leg or the head of the pin.

5. The surgical implant of claim 1, wherein the pin is formed from titanium, stainless steel, or polymers.

6. The surgical implant of claim 1, wherein the radiation source is a biocompatible radioactive material dispersed throughout the pin such that the entirety of the pin irradiates radioactively.

7. The surgical implant of claim 1, wherein the pin is coated with one of gold or a colored oxide layer.

8. The surgical implant of claim 1, wherein the longitudinal leg axis and a longitudinal axis of the first barb define an acute interior angle therebetween.

9. The surgical implant of claim 1, wherein the free distal end of the leg terminates at a pointed tip.

10. The surgical implant of claim 1, wherein the radiation source includes a plurality of brachytherapy capsules.

11. A method of performing a surgical procedure at a target surgical site, the method comprising:
   providing a surgical applier loaded with at least one surgical implant, wherein the at least one surgical implant includes:
   a pin configured for securement to an underlying target surgical site, the pin including:
      a leg defining a longitudinal leg axis and having a proximal end and a free distal end;
      a head extending from the proximal end of the leg along a longitudinal head axis disposed at an angular orientation relative to the longitudinal leg axis and terminating at a free end;
      a first barb extending from the free distal end of the leg at an angular orientation relative to the longitudinal leg axis; and
      a second barb extending from the free end of the head at an angular orientation relative to the longitudinal head axis; and
   a radiation source integrated into or onto the pin;
      placing the surgical applier adjacent to a first location of the target surgical site; and
      firing the surgical applier to secure a first surgical implant of the at least one surgical implant to the first location of the target surgical site;
   wherein the longitudinal head axis and a longitudinal axis of the second barb define an obtuse interior angle therebetween.

12. The method according to claim 11, further comprising:
   relocating the surgical applier to a second location of the target surgical site and re-firing the surgical applier to secure a second surgical implant of the at least one surgical implant to the second location of the target surgical site.

13. The method according to claim 12, wherein the at least one surgical implant includes a plurality of surgical implants, and further comprising:
relocating the surgical applier to a plurality of locations of the target surgical site and re-firing the surgical applier to secure one of the plurality of surgical implants to each respective location of the plurality of locations of the target surgical site.

14. The method according to claim 13, wherein relocating the surgical applier to the plurality of locations of the target surgical site further includes arranging the plurality of surgical implants in any configuration, in any pattern, or in any quantity.

15. The method according to claim 14, wherein providing the surgical applier loaded with the at least one surgical implant includes providing the at least one surgical implant with at least one brachytherapy capsule as the radiation source for providing a dose of radiation to the target surgical site.

16. The method according to claim 11, wherein providing the surgical applier loaded with the at least one surgical implant includes providing the at least one surgical implant with a biocompatible radioactive material dispersed throughout the at least one surgical implant as the radiation source such that the entirety of the at least one surgical implant irradiates radioactively.

17. A surgical applier, comprising:
a handle assembly; and
an endoscopic shaft assembly rotatably supported on and extending from the handle assembly, the endoscopic shaft assembly configured to articulate off-axis, the endoscopic shaft assembly including:
an end effector supported at a distal end of the endoscopic shaft assembly; and
a plurality of surgical implants loaded therein, wherein a distal-most surgical implant of the plurality of surgical implants is disposable in the end effector and is fired by the end effector upon an actuation of the handle assembly, each surgical implant includes:
a pin configured for securement to an underlying target surgical site, the pin including:
a leg defining a longitudinal leg axis and having a proximal end and a free distal end;
a head extending from the proximal end of the leg along a longitudinal head axis disposed at an angular orientation relative to the longitudinal leg axis and terminating at a free end;
a first barb extending from the free distal end of the leg at an angular orientation relative to the longitudinal leg axis; and
a second barb extending from the free end of the head at an angular orientation relative to the longitudinal head axis; and
a radiation source integrated into or onto the pin;
wherein the longitudinal head axis and a longitudinal axis of the second barb define an obtuse interior angle therebetween.

18. The surgical applier according to claim 17, further comprising a cartridge loaded with the plurality of surgical implants, the endoscopic shaft assembly configured to selectively receive the cartridge.

19. The surgical applier according to claim 18, wherein the radiation source is at least one brachytherapy capsule providing a dose of radiation to the target surgical site.

* * * * *